United States Patent [19]
Kitazawa et al.

[11] Patent Number: 5,985,922
[45] Date of Patent: Nov. 16, 1999

[54] AMINO ACID DERIVATIVES AND ACTIVE OXYGEN-RESISTING AGENT

[75] Inventors: Manabu Kitazawa; Kazutami Sakamoto; Keiji Iwasaki, all of Kawasaki, Japan

[73] Assignee: Ajinomoto Co., Inc., Tokyo, Japan

[21] Appl. No.: 09/054,508

[22] Filed: Apr. 3, 1998

[30] Foreign Application Priority Data

Apr. 3, 1997 [JP] Japan .................................. 9-085133

[51] Int. Cl.⁶ .......................... A01N 37/12; A01N 37/18; C07C 229/28
[52] U.S. Cl. ......................... 514/538; 514/620; 560/40; 560/41
[58] Field of Search ....................... 560/40, 41; 514/538, 514/620

[56] References Cited

U.S. PATENT DOCUMENTS

| | | | |
|---|---|---|---|
| 4,254,087 | 3/1981 | Grinstead | 423/24 |
| 4,382,872 | 5/1983 | Grinstead | 252/189 |
| 5,594,012 | 1/1997 | Kitazawa et al. | |

OTHER PUBLICATIONS

Database CAPLUS on STN, Acc. No. 1982:38811, Grinstead, 'Composition and methods for metal extraction,' FR 2462182, abstract, 1982.

Primary Examiner—Gary Geist
Assistant Examiner—Brian J. Davis
Attorney, Agent, or Firm—Oblon, Spivak, McClelland, Maier & Neustadt, P.C.

[57] ABSTRACT

Provided is a novel active oxygen-resisting agent which has an excellent active oxygen resistance and which exhibits a good solubility in an oil solvent. An active oxygen-resisting agent containing as an active ingredient an amino acid derivative represented by the following formula (I)

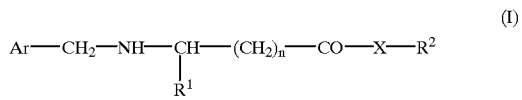

wherein Ar represents a substituted or substituted 2-hydroxyphenyl group or a pyridyl group, said substitution being selected from the group consisting of a halogen atom, a $C_{1-6}$ alkyl group, a hydroxyl group, a hydroxy $C_{1-6}$ alkyl group, a nitro group, a $C_{1-6}$ alkoxyl group or a carboxyl group, $R^1$ represents a side chain of an amino acid, X represents —O— or —NH—, $R^2$ represents a $C_{8-22}$ alkyl group, and n represents 0 or 1, or its salt.

19 Claims, No Drawings

AMINO ACID DERIVATIVES AND ACTIVE OXYGEN-RESISTING AGENT

BACKGROUND OF THE INVENTION

1. Field of the Invention

The present invention relates to a novel amino acid derivative having an excellent active oxygen resistance and exhibiting a good solubility, and an active oxygen-resisting agent comprising the same as an active ingredient.

2. Description of the Related Art

In recent years, various skin disorders and diseases owing to active oxygen species have been reported. For example, it has been known that in aging, canceration, pigmentation and inflammation of the skin by sunlight, especially, ultra-violet light, an active oxygen species deeply participates therein as the cause thereof. Accordingly, if the action of the active oxygen species can be inhibited, it is expected that these disorders and diseases of the skin can be prevented.

Enzymatic antioxidants including superoxide dismutase (SOD), non-enzymatic antioxidants such as ascorbic acid, tocopherol or glutathione, or antioxidant derived from a vegetables, such as tannin are known as substances that inhibits the action of an active oxygen species. However, of these substances, the use of SOD is limited because it is costly and chemically unstable. Also the non-enzymatic antioxidants such as ascorbic acid, tocopherol or glutathione are unstable in many cases, and their effect of inhibiting the active oxygen species is unsatisfactory. The antioxidants derived from the vegetables, such as tannin, are also easily hydrolyzed, and themselves easily oxidized. Accordingly, these substances are problematic in stability in many cases.

Further, in recent years, some investigations have been reported in which a metal ion present in vivo plays a part as a catalyst in the occurrence of the active oxygen species, the occurrence of the active oxygen species is controlled by chelation of the metal ion (for example, Free Radicals in Biology and Medicine, Oxford, Clarendon Press, p. 234, 1989). As a compound having a chelation ability, a disferrioxamine compound is known. Since this compound is, however, too strong a chelator, the balance of the metal ion in vivo is interfered with, and this compound is costly. Besides the disferrioxamine compound, metal ion chelating agents such as 2,2'-dipyridyl, 1,10-phenanthrolene and 2,2'-dipyridylamine have been studied. However, most of these compounds exhibit skin irritation.

Amino acid derivatives which are stable, which show low skin irritation and which have an excellent active oxygen resistance are reported in WO 94/14755 (U.S. Pat. No. 5,594,012). Nevertheless, since the derivatives have a low solubility in a multi-purpose oil solvent such as liquid paraffin or an olive oil, the use thereof is limited.

SUMMARY OF THE INVENTION

It is an object of the present invention to provide a novel active oxygen-resisting agent which has an excellent active oxygen resistance and which exhibits a good solubility in an oil solvent.

The present invention relates to an active oxygen-resisting agent containing as an active ingredient an amino acid derivative represented by formula (I).

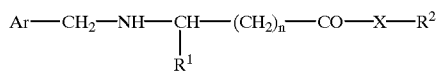

wherein
Ar represents a substituted or unsubstituted 2-hydroxyphenyl group or a pyridyl group, said substitution being selected from the group consisting of a halogen atom, a $C_{1-6}$alkyl group, a hydroxyl group, a hydroxy $C_{1-6}$allyl group, a nitro group, a $C_{1-6}$alkoxyl group or a carboxyl group,
$R^1$ represents a side chain of an amino acid,
X represents —O— or —NH—,
$R^2$ represents a $C_{8-22}$alkyl group, and
n represents 0 or 1, or a salt thereof.

The amino acid derivative represented by the above-mentioned formula (I) is a novel compound, which is not described in the literature.

DETAILED DESCRIPTION OF THE PREFERRED EMBODIMENTS

In the amino acid derivative represented by the above-mentioned formula (I), $R^1$ includes side chains of acidic amino acids such as glutamic acid, aspartic acid, cysteic acid and homocysteic acid, neutral amino acids such as glycine, alanine, β-alanine, valine, leucine, isoleucine, phenylalanine, tryptophan, threonine, serine, homoserine, tyrosine, cysteine, methionine, glutamine and asparagine, and basic amino acids such as lysine, ornithine, arginine and histidine. The neutral amino acids are preferable, and glycine, alanine and phenylalanine are especially preferable.

When an asymmetric carbon atom is present in the amino acid residue, an optically active substance or a racemic substance is available. Examples of the salt include inorganic acid salts such as a hydrochloride and a sulfate; and organic acid salts such as an acetate, a tartrate, a citrate, a p-toluenesulfonate, a fatty acid salt, an acidic amino acid salt and a pyroglutamate. These may be incorporated as amino acid derivative salts, or the amino acid derivatives and the bases may be incorporated separately to form amino acid derivative salts in the composition.

Within the context of the present invention, the group Ar is a 2-hydroxylphenyl group or a pyridyl group which may be substituted on the aromatic ring by one or more substituents selected from the group consisting of a halogen atom, a $C_{1-6}$alkyl group, a hydroxyl group, a hydroxy $C_{1-6}$alkyl group, a nitro group, a $C_{1-6}$alkoxyl group or a carboxyl group.

The amino acid derivative represented by the abovementioned formula (I) can easily be prepared by conventional methods known to those of ordinary skill in the art. For example, amino acid derivatives maybe prepared by reacting 2-hydroxy aromatic aldehyde such as salicylaldehyde with an amino acid long-chain alkyl ester or an amino acid long-chain alkylamide in the presence or absence of a solvent, and followed by reduction such as by adding thereto a hydrogenation agent such as sodium borohydride. Or, it can also be introduced by reacting a 2-hydroxy aromatic aldehyde with an amino acid to form a Schiff base, adding thereto a hydrogenation agent such as sodium borohydride to obtain N-(2-hydroxy aromatic-1-methylene)amino acid, and then subjecting the same to esterification or amidation. The 2-hydroxy aromatic aldehyde used herein includes salicylaldehyde as well as 2-hydroxy-1-naphthoaldehyde, pyridoxal, 2-hydroxy-4-methoxybenzaldehyde, o-vanillin, 5-bromosalicylaldehyde, 5-chlorosalicylaldehyde, 5-nitrosalicylaldehyde, 3,5 -dibromosalicylaldehyde, 3,5-dichlorosalicylaldehyde, 2,3-dihydroxybenzaldehyde, 2,4-dihydroxybenzaldehyde and 2,5-dihydroxybenzaldehyde.

The active oxygen-resisting agent of the present invention may be used by administration directly to a system where active oxygen is generated. Within the context of the present invention active oxygen species include hydoxyl radicals, singlet oxygen, and superoxide radical anions.

Though the anti-active oxygen compounds of the general formula (I) according to this invention may be directly administered to active oxygen generating systems, for example, intravenously, skin-topically, etc., they are usually incorporated in cosmetics such as lotion and cream; pharmaceuticals such as anti-inflammatory agent and antiarteriosclerotic agent; and foods such as edible oil. For use as the anti-skin aging component in cosmetics for example, they should be naturally comprised in an amount producing anti-skin aging activities, and may be comprised in an amount of, for example, 0.1 to 10% of the total weight of the cosmetics. For pharmaceutical use in human bodies, they should be naturally administered in an amount producing an intended effect, and may be administered in an amount of, for example, 0.1 to 1000 mg/day per adult. In order to prevent denaturation or deterioration of foods, they may be similarly added to the foods in an amount of 0.1 to 10% of the weight thereof. Otherwise, the anti-active oxygen compounds according to this invention may be formulated into special anti-skin aging preparations, e.g., in the form of ointment, instead of being incorporated in cosmetics.

Generally, the active agent is applied topically to a surface where active oxygen is generated, such as skin or hair. It is ordinarily to be used by being incorporated in toiletries or a skin external agent. For example, when this agent is incorporated into toiletries as an antioxidant, it may be added in an amount of from 0.01 to 10% by weight, preferably 0.1 to 3% by weight, more preferably 0.5 to 2% by weight. Further, when it is incorporated into a skin external agent, it is appropriate that the amount is from 0.01 to 50% by weight.

When the active oxygen-resisting agent of the present invention is used by incorporation into toiletries or a skin external agent, ingredients which are generally used in toiletries or a skin external agent can be added, besides the active oxygen-resisting agent of the present invention, unless the effects of the present invention are inhibited. Examples of the ingredients which are generally used in toiletries or a skin external agent include urea, ethanol, isopropanol, a polyhydric alcohol, an anionic surfactant, an ampholytic agent, a nonionic surfactant, a cationic surfactant, an oil, a high-molecular compound, an emulsifying agent, a powder and an antibiotic.

Suitable carriers for the composition comprise an oil such a olive oil or paraffin oil.

The form of the toiletries or the skin external agent containing the active oxygen-resisting agent of the present invention is not particularly limited, and this agent may take any form of a solution, a paste, a gel, a solid, a powder and the like. Further, the toiletries or the skin external agent containing the active oxygen-resisting agent of the present invention can find use in toiletries or washing agents such as an oil, a lotion, a cream, an emulsion, a gel, a shampoo, a hair rinse, a hair conditioner, an enamel, a foundation, a lipstick, a face powder, a pack, an ointment, a perfume, a powder, an eau de Cologne, a soap, an aerosol and a cleansing foam, as well as in an agent for preventing or improving skin ageing, an agent for preventing or improving skin inflammation, a bath agent, a hair growing agent, a skin care solution, an antisunburn agent and an agent for preventing or improving a skin roughness due to a trauma, chaps and cracks.

The other ordinary ingredients in toiletries or a skin external agent can be added to the toiletries or the skin external agent containing the active oxygen-resisting agent of the present invention. Examples of the ordinary ingredients in toiletries or a skin external agent include a wetting agent such as sodium DL-pyrolidonecarboxylate or sodium lactate; a chelating agent such as ethylenediaminetetraacetic acid, citric acid, ascorbic acid, maleic acid, succinic acid, cephalin, saccharinic acid, hexametaphosphoric acid, 1-hydroxyethane-1,1-diphosphonic acid, dihydroxyethylglycine or salts thereof, a crude drug; vitamins; hormones; an agent such as an antihistamic agent or a skin astringent; a hair growth accelerator such as cantharis tincture, capsicum tincture, ginger tincture, swertiae extract, garlic extract, hinokithiol, carpronium chloride, pentadecanoic acid glyceride, estrogen or various light-sensitive elements; a beautifier such as arbutin or other hydroquinone glycosides; an antioxidant such as dibutylhydroxytoluene, butylhydroxyanisole, propyl gailate or tocopherol; an animal or vegetable extract such as a placenta extract, elastin, collagen, an aloe extract, a hamamelis extract, a sponge cucumber extract, a camomile extract or a licorice extract; an antiseptic such as cresol derivatives or paraben derivatives; a hormone such as corticosteroid; an amino acid; a softener; a demulcent; a tough improver; a superfatting agent; a viscosity modifier; a pearling agent; an antiinflammatory agent; an ultraviolet absorber; a pH adjustor; a flavor; and a coloring material.

The present invention is illustrated more specifically by referring to the following Examples. However, the present invention is not limited to these Examples. In Examples, the amount was expressed by % by weight of the total weight of the composition.

SYNTHESIS EXAMPLE 1

Synthesis of N-(2-hydroxybenzyl)-L-alanine lauryl ester

L-alanine (2.9 g) was dissolved in 20 ml of a 2-N sodium hydroxide aqueous solution, and 3.5 ml of salicylaldehyde and 0.4 g of sodium borohydride were then added thereto in this order. After the mixture was stirred for 1 hour, 3.5 ml of salicylaldehyde and 0.4 g of sodium borohydride were added thereto again. The mixture was stirred at room temperature for 1 hour, and the insoluble matter was then separated through filtration. The filtrate was extracted with diethyl ether. The pH was adjusted to 6 with hydrochloric acid to obtain 5.8 g of N-(2-hydroxybenzyl)-L-alanine. The resulting N-(2-hydroxybenzyl)-L-alanine (4.6 g) and 8.8 g of 1-dodecanol were added to 150 ml of toluene, and a hydrogen chloride gas was blown thereto up to the saturation. Ten grams of a molecular sieve were added thereto, and the mixture was stirred overnight. After the insoluble matter was separated through filtration, the filtrate was concentrated, and the resulting oil was dissolved in methylene chloride. The mixture was washed with a saturated aqueous solution of sodium chloride. The resulting mixture was dried over magnesium sulfate, and concentrated under reduced pressure to give 8 g of N-(2-hydroxybenzyl)-L-alanine lauryl ester.

High resolution mass spectrum (M+H$^+$): calculated: 364.2852, found: 364.2849 $^1$H-NMR, [CDCl$_3$] δ: 0.86 (t, 3H), 1.20–1.38 (m, 18H), 1.37 (d, 3H), 1.55 (m, 2H), 3.42 (q, 1H), 3.63 (6, 2H), 3.93 (dd, 2H), 6.77 (t, 1H), 6.86 (d, 1H), 6.96 (d, 1H), 7.17 (t, 1H)

SYNTHESIS EXAMPLE 2

Synthesis of N-(2-hydroxybenzyl)-L-alanine stearyl ester

The above-mentioned compound was prepared in an analogous manner to Synthesis Example 1.

High resolution mass spectrum (M+H$^+$) calculated: 448.3791, found: 448.3802 $^1$H-NMR [CDCl$_3$] δ: 0.86 (t, 3H), 1.19–1.38 (m, 30H), 1.37 (d, 3H), 1.56 (m, 2H), 3.51 (q, 1H), 3.63 (t, 2H), 4.01 (dd, 2H), 6.79 (t, 1H), 6.91 (d, 1H)), 7.03 (d, 1H), 7.18 (t, 1H)

SYNTHESIS EXAMPLE 3

Synthesis of N-(2-hydroxybenzyl)glycine lauryl ester

The above-mentioned compound was prepared in an analogous manner to Synthesis Example 1.

High resolution mass spectrum (M+H$^+$) calculated: 350.2695, found: 350.2685

SYNTHESIS EXAMPLE 4

Synthesis of N-(2-hydroxybenzyl)-L-phenylalanine lauryl ester

The above-mentioned compound was prepared in an analogous manner to Synthesis Example 1.

High resolution mass spectrum (M+H$^+$): calculated: 440.3165, found: 440.3165

SYNTHESIS EXAMPLE 5

Synthesis of N-(2-hydroxybenzyl)-L-alanine laurylamide

L-alanine laurylamide (2.5 g) and 1 g of sodium hydroxide were dissolved in 20 ml of methanol, and 1.0 ml of salicylaldehyde and 0.1 g of sodium borohydride were added thereto in this order. After the mixture was stirred for 1 hour, 1.0 ml of salicylaldehyde and 0.1 g of sodium borohydride were added thereto again in this order. The mixture was stirred overnight at room temperature, and the insoluble matter was then separated through filtration. The filtrate was adjusted to a pH of 7 with hydrochloric acid, and concentrated under reduced pressure. The resulting oil was dissolved in diethyl ether, washed with water, and then dried over with magnesium sulfate. After the drying agent was separated through filtration, the filtrate was concentrated under reduced pressure to give 3 g of N-(2-hydroxybenzyl)-L-alanine laurylamide.

High resolution mass spectrum (M+H$^+$): calculated: 363.3012, found: 363.2972 $^1$H-NMR, [CDCl$_3$] δ: 0.88 (t, 3H), 1.23–1.35 (m, 18H) 1.50 (m, 2H), 3.13 (q, 1H), 3.27 (t, 2H), 3.91 (dd, 2H), 6.78 (t, 1H), 6.83 (d, 1H), 6.96 (d, 1H), 7.19 (t, 1H)

SYNTHESIS EXAMPLE 6

Synthesis of N-(2-hydroxybenzyl)-L-alanine stearylamide

The above-mentioned compound was prepared in an analogous manner to Synthesis Example 5.

High resolution mass spectrum (M+H$^+$) calculated: 447.3951, found: 447.3946 $^1$H-NMR [CDCl$_3$] δ: 0.87 (t, 3H), 1.23–1.36 (m, 30H), 1.38 (d, 3H), 1.51 (m, 2H), 3.23 (q, 1H), 3.33 (t, 2H), 3.97 (dd, 2 H), 6.78 (t, 1H), 6.88 (d, 1H), 7.00 (d, 1H), 7.18 (t, 1H)

SYNTHESIS EXAMPLE 7

Synthesis of N-(2-hydroxybenzyl)glycine laurylamide

The above-mentioned compound was prepared in an analogous manner to Synthesis Example 5.

High resolution mass spectrum (M+H$^+$) calculated: 349.2855, found: 349.2865

SYNTHESIS EXAMPLE 8

Synthesis of N-(2-hydroxybenzyl)phenylalanine laurylamide

The above-mentioned compound was prepared in an analogous manner to Synthesis Example 5.

High resolution mass spectrum (M+H$^+$): calculated: 439.3325, found: 439.3316

SYNTHESIS EXAMPLE 9

Synthesis of N-(2-hydroxybenzyl)-L-alanine octylamide

The above-mentioned compound was prepared in an analogous manner to Synthesis Example 5.

High resolution mass spectrum (M+H$^+$) calculated: 307.2386, found: 307.2377

TEST EXAMPLE 1

Test for an Active Oxygen Resistance

The test was conducted according to the method described in Method in Enzymol., vol. 52, p. 302, 1978 (described also in Test Example 3 of Japanese Patent Laid-Open No. 814, 755/1994 and Test Example 3 of WO 94/14755). The outline of the test method was that a homogenized 20-mM phosphate buffer of the whole brain of a C57 black mouse was prepared, a test substance was added thereto, and an absorbance of the mixture was measured. A percent inhibition of lipid peroxidation of the test compound was calculated according to the following formula (II) The results are shown in Table 1.

Percent peroxidation inhibition (%)—

$$\{1-(A_1-A_3)/(A_2-A_3)\}\times 100 \quad (II)$$

A$_1$: Absorbance in the addition of the test compound

A$_2$: Absorbance before the addition of the test compound

A$_3$: Absorbance when the test compound is not added, nor is the heating at 37° C. for 30 minutes conducted.

TABLE 1

| Test compound | Percent inhibition (%) |
|---|---|
| Compound in Synthesis Example 1 | 39 |
| Compound in Synthesis Example 2 | 16 |
| Compound in Synthesis Example 5 | 80 |
| Compound in Synthesis Example 6 | 17 |
| N-(2-hydroxybenzyl)-L-alanine | 6 |
| Vitamin C | −23 |
| Citric acid | −15 |

As shown in Table 1, the compounds of the present invention exhibit a higher percent inhibition of lipid peroxidation than vitamin C and citric acid as a multi-purpose antioxidant, providing a high active oxygen resistance.

TEXT EXAMPLE 2

Test for a Solubility

The solubility in the solvent shown in Table 2 when the concentration was 1% by weight was evaluated.

TABLE 2

| Test compound | Olive oil | Liquid paraffin |
|---|---|---|
| Compound in Synthesis Example 1 | soluble | soluble |
| Compound in Synthesis Example 2 | soluble | soluble |
| Compound in Synthesis Example 3 | soluble | soluble |
| Compound in Synthesis Example 4 | soluble | soluble |
| Compound in Synthesis Example 5 | soluble | gelling |
| Compound in Synthesis Example 6 | soluble | gelling |
| Compound in Synthesis Example 7 | soluble | gelling |
| Compound in Synthesis Example 8 | soluble | gelling |
| N-(2-hydroxybenzyl)-L-alanine | insoluble | insoluble |
| N-(2-hydroxybenzyl)-L-glycine | insoluble | insoluble |
| N-(2-hydroxybenzyl)-L-phenylalanine | insoluble | insoluble |

As shown in Table 2, the compounds of the present invention are easily soluble in a multi-purpose olive oil of toiletries or a skin external agent by introducing a long-chain alkyl group, and are also dissolved or uniformly dispersed in liquid paraffin.

TEXT EXAMPLE 3

Organoleptic Test

The compounds were subjected as a skin external agent to organoleptic evaluation by panelists, 10 men and 10 women to estimate the feeling upon use. Table 3 shows the evaluation standard of each evaluation item. Compounds shown in Table 4 were prepared in the organoleptic evaluation.

TABLE 3

| Evaluation item | Explanation | |
|---|---|---|
| Sticky feeling (face) | ⊙: very clean<br>Δ: sticky | o: clean<br>x: very sticky |
| Sticky feeling (hands) | ⊙: very clean<br>Δ: sticky | o: clean<br>x: very sticky |
| Dry and hard feeling (face) | ⊙: very smooth<br>Δ: dry and hard | o: smooth<br>x: very dry and hard |
| Dry and hard feeling (hands) | ⊙: very smooth<br>Δ: dry and hard | o: smooth<br>x: very dry and hard |

TABLE 4

| Test Compound | Examples | | | Comparative Examples | | |
|---|---|---|---|---|---|---|
| | 1 | 2 | 3 | | | |
| Compound in Synthesis Example 1 | 0.1 | 1.0 | 5.0 | | | |
| N-(2-hydroxybenzyl)-L-alanine | | | | 1.0 | 5.0 | 1 |
| Liquid paraffin | 30.0 | 30.0 | 30.0 | 30.0 | 30.0 | |
| Diglycerol dioleate | 5.0 | 5.0 | 5.0 | 5.0 | 5.0 | 5.0 |
| Propylene glycol | 5.0 | 5.0 | 5.0 | 5.0 | 5.0 | 5.0 |
| Water | balance | balance | balance | balance | balance | balance |
| Evaluation Sticky feeling (face) | o | ⊙ | ⊙ | Δ | o | x |
| Sticky feeling (hands) | o | ⊙ | ⊙ | o | ⊙ | x |
| Dry and hard feeling (face) | ⊙ | ⊙ | ⊙ | x | x | o |
| Dry and hard feeling (hands) | ⊙ | ⊙ | ⊙ | o | Δ | o |

As shown in Table 4, the compounds of the present invention were all free from the sticky feeling and the dry and hard feeling, and the feeling upon use thereof was quite satisfactory.

EXAMPLE 4

A hair growth accelerator having a composition shown in Table 5 was prepared in a usual manner. The product was free from the sticky feeling and the dry and hard feeling, and the feeling upon use thereof was quite satisfactory.

TABLE 5

| Ingredients | Amount |
| --- | --- |
| Compound in Synthesis Example 3 | 0.1 |
| Carpronium chloride | 1 |
| Pantotenyl ethyl ether | 0.5 |
| Diphenhydramine chloride | 0.1 |
| DL-α-tocopherol | 0.1 |
| Hinokithiol | 0.1 |
| Salicylic acid | 0.2 |
| L-menthol | 0.2 |
| Glycyrrhetinic acid | 0.2 |
| Sodium DL-pyrolidonecarboxylate | 1 |
| Ethanol | 50 |
| Water | balance |
| Total | 100 |

EXAMPLE 5

Dentifrice

A dentifrice having a composition shown in Table 6 was prepared in a usual manner. The product was free from the sticky feeling and the dry and hard feeling, and the feeling upon use thereof was quite satisfactory.

TABLE 6

| Ingredients | Amount |
| --- | --- |
| Compound in Synthesis Example 1 | 0.2 |
| Calcium hydrogenphosphate | 45 |
| Silicic anhydride | 5 |
| Glycerin | 8 |
| Sorbitol | 10 |
| Caroboxymethyl cellulose | 1 |
| Sodium lauryl sulfate | 1.2 |
| Saccharin | 0.1 |
| Pigment | suitable amount |
| Antiseptic and pharmaceutical ingredient | suitable amount |
| Flavor | suitable amount |
| Water | balance |
| Total | 100 |

EXAMPLE 6

Mouth Wash

A mouth wash having a composition shown in Table 7 was prepared in a usual manner. The product was free from the sticky feeling and the dry and hard feeling, and the feeling upon use thereof was quite satisfactory.

TABLE 7

| Ingredients | Amount |
| --- | --- |
| Compound in Synthesis Example 3 | 0.2 |
| Ethanol | 40 |
| Polyoxyethylene hardened castor oil | 1 |
| Glycerin | 10 |
| 1-Menthol | 0.5 |
| Sodium saccharine | 0.1 |
| Chlorhexidine gluconate | suitable amount |
| Flavor | suitable amount |
| Water | balance |
| Total | 100 |

EXAMPLE 7

Anti-sunburn Cream

An anti-sunburn cream having a composition shown in Table 8 was prepared in a usual manner. The product was free from the sticky feeling and the dry and hard feeling, and the feeling upon use thereof was quite satisfactory.

TABLE 8

| Ingredients | Amount |
| --- | --- |
| Compound in Synthesis Example 1 | 1.2 |
| Glycerin | 5 |
| Stearyl alcohol | 1 |
| Sesame oil | 2 |
| Ultraviolet absorber | 5 |
| Stearic acid | 5.5 |
| Monostearic acid glycerin | 10 |
| Antiseptic and antioxidant | suitable amount |
| Flavor | suitable amount |
| Water | balance |
| Total | 100 |

EXAMPLE 8

Acne Lotion

An acne lotion having a composition shown in Table 9 was prepared in a usual manner. The product was free from the sticky feeling and the dry and hard feeling, and the feeling upon use thereof was quite satisfactory.

TABLE 9

| Ingredients | Amount |
| --- | --- |
| Compound in Synthesis Example 2 | 0.01 |
| Compound in Synthesis Example 4 | 0.01 |
| Thioxolone | 0.01 |
| Homosulfamine | 0.5 |
| Hexachlorophene | 0.01 |
| d-Camphor | 0.02 |
| 1-Menthol | 0.05 |
| 1,3-Butylene glycol | 5 |
| Ethanol | 15 |
| Flavor | suitable amount |
| Water | balance |
| Total | 100 |

EXAMPLE 9

Beautifier

A beautifier having a composition shown in Example 10 was prepared in a usual manner. The product was free from the sticky feeling and the dry and hard feeling, and the feeling upon use thereof was quite satisfactory.

TABLE 10

| Ingredients | Amount |
| --- | --- |
| Compound in Synthesis Example 2 | 0.5 |
| Arbutin | 0.5 |
| Vaseline | 2.5 |
| Liquid paraffin | 10 |
| Cetostearyl alcohol | 12 |
| Polyoxyethylene (20 E.O.) sorbitan monostearate | 7 |
| Sorbitan monostearate | 1 |
| Propylene glycol | 5 |
| Antiseptic and flavor | suitable amount |
| Water | balance |
| Total | 100 |

EXAMPLES 10 to 13

Ointment

Ointments having compositions shown in Tables 11 to 14 were prepared in a usual manner. The products were free from the sticky feeling and the dry and hard feeling, and the feeling upon use thereof was quite satisfactory.

TABLE 11

| Ingredients | Amount |
| --- | --- |
| Compound in Synthesis Example 3 | 0.5 |
| Bacitracin | suitable amount |
| Polymyxin sulfate | suitable amount |
| Polyethylene glycol distearate | 15 |
| Methyl p-oxybenzoate | 0.1 |
| Vaseline | balance |
| Total | 100 |

TABLE 12

| Ingredients | Amount |
| --- | --- |
| Compound in Synthesis Example 2 | 0.5 |
| Ethyl aminobenzoate | 10 |
| Boric acid | 4 |
| Zinc oxide | 9 |
| glycerin | 4 |
| Beeswax | 20 |
| vegetable oil | balance |
| Total | 100 |

TABLE 13

| Ingredients | Amount |
| --- | --- |
| Compound in Synthesis Example 4 | 0.5 |
| Pyridoxine hydrochloride | 1 |
| Vaseline | 25 |
| Stearyl alcohol | 25 |
| Propylene glycol | 12 |
| Sodium laurate | 1 |
| Antiseptic | suitable amount |
| Water | balance |
| Total | 100 |

TABLE 14

| Ingredients | Amount |
| --- | --- |
| Compound in synthesis Example 1 | 0.5 |
| Hydrocortisone acetate | 1 |
| Antiseptic | suitable amount |
| Vaseline | 25 |
| Stearyl alcohol | 25 |
| Propylene glycol | 12 |
| Sodium laurate | 1 |
| Antiseptic | suitable amount |
| Water | balance |
| Total | 100 |

EXAMPLES 14 to 16

Liquid Shampoo

Liquid shampoos having compositions shown in Tables 15 to 17 were prepared in a usual manner. The products were free from the sticky feeling and the dry and hard feeling, and the feeling upon use thereof was quite satisfactory.

TABLE 15

| Ingredients | Amount |
| --- | --- |
| Compound in Synthesis Example 1 | 0.1 |
| Potassium N-lauroylglutamate | 5 |
| Potassium laurate | 1 |
| N-lauroyl-N-methyl-β-alanine sodium salt | 5 |
| Lauryl ether sodium sulfate | 2 |
| Lauroyl diethanolamide | 3 |
| Carboxyvinyl polymer | 2 |
| Collagen hydrolyzate | 1 |
| Sodium pyrolidonecarboxylate | 6 |
| Citric acid | 1 |
| Squalene | 0.5 |
| Phenoxyethanol | 0.2 |
| Methyl paraben | 0.1 |
| Disodium methylenediaminetetraacetate | 0.2 |
| Flavor | suitable amount |
| Water | balance |
| Total | 100 |

TABLE 16

| Ingredients | Amount |
| --- | --- |
| Compound in Synthesis Example 3 | 1 |
| Triethanolamine lauryl sulfate | 30 |
| Polyoxyethylene (3 E.O.) lauryl ether triethanolamine sulfate | 5 |
| Lauryldimethyl aminoacetate betaine | 8 |
| Coconut oil fatty acid amide propyl betaine | 2 |
| Diethanolamide laurate | 4 |
| Hydroxyethyl cellulose | 1 |
| Polyoxyethylene (30 E.O.) hardened castor oil | 1 |
| Glycyrrhetinic acid dipotassium salt | 0.2 |
| Dibutylhydroxytoluene | 0.2 |
| Zinc pyrithione | 2 |
| Disodium ethylenediaminetetraacetate | 0.1 |
| Flavor | suitable amount |
| Water | balance |
| Total | 100 |

TABLE 17

| Ingredients | Amount |
| --- | --- |
| Compound in Synthesis Example 4 | 2 |
| Disodium lauryl sulfosuccinate | 5 |
| Sodium dodecylbenzenesulfonate | 3 |
| Sodium lauryl phosphate | 3 |
| Triethanolamine laurate | 10 |
| Triethanolamine myristate | 10 |
| Laurylimidazolinium betaine | 5 |
| Lauroyldiethanolamide | 6 |
| Propylene glycol | 7 |
| Lauryldimethylamine oxide | 2 |
| Antiseptic | suitable amount |
| Flavor | suitable amount |
| Water | balance |
| Total | 100 |

EXAMPLE 17

Rinse

A rinse having a composition shown in Table 18 was prepared in a usual manner. The product was free from the sticky feeling and the dry and hard feeling, and the feeling upon use thereof was quite satisfactory.

TABLE 18

| Ingredients | Amount |
| --- | --- |
| Compound in Synthesis Example 1 | 0.1 |
| Liquid paraffin | 2 |
| Lanolin alcohol | 1 |
| Vaseline | 2 |
| Cetyl alcohol | 2 |
| Glycerin monostearate | 2 |
| Polyethylene glycol (100) stearate | 2 |
| Polyoxyethylene (2 E.O.) cetyl ether | 1 |
| Polyoxyethylene (10 E.O.) octylphenyl ether | 0.5 |
| Plantalene 1200 ™ (made by Henkel) | 1 |
| Xanthan gum | 0.2 |
| Collagen hydrolyzate | 3 |
| Lauryltrimethylammonium chloride | 4 |
| Nε-lauroyl-L-lysine ethyl ester hydrochloride | 1 |
| Citric acid | suitable amount |
| 1,3-Butylene glycol | 5 |
| Flavor | suitable amount |
| Lauryldimethylbenzylammonium chloride | suitable amount |
| Antioxidant | suitable amount |
| Water | balance |
| Total | 100 |

EXAMPLE 18

Cleansing Foam

A cleansing foam having a composition shown in Table 19 was prepared in a usual manner. The product was free from the sticky feeling and the dry and hard feeling, and the feeling upon use thereof was quite satisfactory.

TABLE 19

| Ingredients | Amount |
| --- | --- |
| Compound in Synthesis Example 2 | 3 |
| Sodium myristate | 15 |
| Potassium stearate | 20 |
| Cetanol | 3 |
| Lanolin | 1 |
| 1,3-Butylene glycol | 5 |
| Glycerin | 10 |
| Potassium hydroxide | 5 |
| Antiseptic | 0.1 |
| Flavor | 0.1 |
| Water | balance |
| Total | 100 |

EXAMPLE 19

Lotion

A lotion having a composition shown in Table 20 was prepared in a usual manner. The product was free from the sticky feeling and the dry and hard feeling, and the feeling upon use thereof was quite satisfactory.

TABLE 20

| Ingredients | Amount |
| --- | --- |
| Compound in Synthesis Example 4 | 0.1 |
| Ethanol | 36 |
| Citric acid | 0.2 |
| Zinc p-phenylsulfonate | 0.2 |
| Dipropylene glycol | 3 |
| Ethyl aminobenzoate | 0.2 |

TABLE 20-continued

| Ingredients | Amount |
| --- | --- |
| Menthol | 0.3 |
| Flavor | 0.1 |
| Antiseptic | 0.1 |
| Water | balance |
| Total | 100 |

EXAMPLES 20 to 22

Beauty Cream

Beauty creams having compositions shown in Tables 21 to 23 were prepared in a usual manner. The products were free from the sticky feeling and the dry and hard feeling, and the feeling upon use thereof was quite satisfactory.

TABLE 21

| Ingredients | Amount |
| --- | --- |
| Compound in Synthesis Example 2 | 0.1 |
| Stearic acid | 18 |
| Liquid paraffin | 2 |
| Jojoba oil | 0.5 |
| Sorbitan monoleate | 2 |
| Potassium hydroxide | 1 |
| Sorbitol | 6 |
| Flavor | 0.1 |
| Antiseptic | 0.1 |
| Water | balance |
| Total | 100 |

TABLE 22

| Ingredients | Amount |
| --- | --- |
| Compound in Synthesis Example 3 | 0.2 |
| Stearic acid | 8 |
| Cetyl palmitate | 2 |
| Cetanol | 3 |
| Beeswax | 1 |
| Vaseline | 1 |
| Liquid paraffin | 14 |
| Silicone oil | 1 |
| Polyoxyethylene (20 E.O.) sorbitan stearate | 1 |
| Triethanolamine | 1 |
| Propylene glycol | 5 |
| "Prodew 100" ™ (wetting agent of Ajinomoto) | 2 |
| Flavor | 0.1 |
| Antiseptic | 0.1 |
| Water | balance |
| Total | 100 |

TABLE 23

| Ingredients | Amount |
| --- | --- |
| Compound in Synthesis Example 4 | 0.1 |
| Stearic acid | 14 |
| Beeswax | 2 |
| Liquid paraffin | 1 |
| Polyoxyethylene (20 E.O.) cetyl ether | 5 |
| Polyethylene glycol (25) monostearate | 6 |
| Allantoin chlorohydroxyammonium | 0.1 |
| Propylene glycol | 5 |
| Flavor | 0.1 |

TABLE 23-continued

| Ingredients | Amount |
| --- | --- |
| Antiseptic | 0.1 |
| Water | balance |
| Total | 100 |

EXAMPLE 23

Face wash

A face wash having a composition shown in Table 24 was prepared in a usual manner. The product was free from the sticky feeling and the dry and hard feeling, and the feeling upon use thereof was quite satisfactory.

TABLE 24

| Ingredients | Amount |
| --- | --- |
| Compound in Synthesis Example 1 | 2 |
| Triethanolamine N-lauroylglutamate | 25 |
| Triethanolamine laurate | 5 |
| Polyoxypropylene (11) polyoxyethylene (4) butyl ether (HLB 7.2) | 6 |
| Dibutylhydroxytoluene | 0.2 |
| Ethanol | 3 |
| Flavor | 0.3 |
| Water | balance |
| Total | 100 |

EXAMPLE 24

Cleansing Foam

A cleansing foam having a composition shown in Table 25 was prepared in a usual manner. The product was free from the sticky feeling and the dry and hard feeling, and the feeling upon use thereof was quite satisfactory.

TABLE 25

| Ingredients | Amount |
| --- | --- |
| Compound in Synthesis Example 2 | 2 |
| Liquid paraffin | 35 |
| Ceresin | 8 |
| Beeswax | 8 |
| Cetyl i-octanoate | 4 |
| Di(cholesterol, behenyl, octyldodecylalcohol)-N-lauroyl-L-glutamate | 2 |
| Sorbitan sesquioleate | 2 |
| Polyoxyethylene (20 E.O.) sorbit beeswax | 5 |
| Sorbitol | 5 |
| Antioxidant | 0.1 |
| Antiseptic | 0.1 |
| Water | balance |
| Total | 100 |

EXAMPLE 25

Emulsion

An emulsion having a composition shown in Table 26 was prepared in a usual manner. The product was free from the sticky feeling and the dry and hard feeling, and the feeling upon use thereof was quite satisfactory.

TABLE 26

| Ingredients | Amount |
| --- | --- |
| Compound in Synthesis Example 4 | 0.2 |
| Lauric acid | 0.1 |
| Stearic acid | 0.5 |
| Cetostearyl alcohol | 0.5 |
| Glycerin triisooctanoate | 4 |
| Avocado oil | 4 |
| Polyoxyethylene (60 E.O.) sorbitan monooleate | 1.5 |
| Glycerin monostearate | 0.5 |
| Xanthan gum (2-% aqueous solution) | 7 |
| 1,3-Butylene glycol | 5 |
| Ascorbic acid | suitable amount |
| Flavor | suitable amount |
| Antiseptic | 0.1 |
| Water | balance |
| Total | 100 |

EXAMPLE 26

Lipstick

A lipstick having a composition shown in Table 27 was prepared in a usual manner. The product was free from the sticky feeling and the dry and hard feeling, and the feeling upon use thereof was quite satisfactory.

TABLE 27

| Ingredients | Amount |
| --- | --- |
| Compound in Synthesis Example 2 | 0.5 |
| Beeswax | 5 |
| Carnauba wax | 2 |
| Candelilla wax | 6 |
| Ceresin | 7 |
| Microcrystalline wax | 3 |
| Lanolin | 8 |
| Octyldodecyl oleate | 12 |
| Isopropyl myristate | 8 |
| Titanium oxide | 2 |
| Organic pigment (tar pigment) | 5 |
| Polyglycerin | 1 |
| Antioxidant | suitable amount |
| Antiseptic and flavor | suitable amount |
| Castor oil | balance |
| Total | 100 |

EXAMPLE 27

Hair Conditioner

A hair conditioner having a composition shown in Table 28 was prepared in a usual manner. The product was free from the sticky feeling and the dry and hard feeling, and the feeling upon use thereof was quite satisfactory.

TABLE 28

| Ingredients | Amount |
| --- | --- |
| Compound in Synthesis Example 1 | 0.1 |
| Liquid paraffin | 2 |
| Lanolin alcohol | 1 |
| Vaseline | 2 |
| Cetyl alcohol | 2 |
| Glycerin monostearate | 2 |
| Polyethylene glycol (100) stearate | 2 |
| Polyoxyethylene (2 E.O.) cetyl ether | 1 |

TABLE 28-continued

| Ingredients | Amount |
| --- | --- |
| Polyoxyethylene (10 E.O.) oxtylphenyl ether | 0.5 |
| Plantalene 1200 ™ (made by Henkel) | 1 |
| Xanthan gum | 0.2 |
| Collagen hydrolyzate | 3 |
| Lauryltrimethylammonium chloride | 4 |
| Nε-lauroyl-L-lysine ethyl ester hydrochloride | 1 |
| Citric acid | suitable amount |
| 1,3-Butylene glycol | 5 |
| Flavor | suitable amount |
| Lauryldimethylbenzylammonium chloride | suitable amount |
| Antioxidant | suitable amount |
| Water | balance |
| Total | 100 |

The novel active oxygen-resisting agent of the present invention has an excellent active oxygen resistance, and exhibits a good solubility in an oil solvent. Further, toiletries or an external agent containing the active oxygen resisting agent remains effectively on the skin, is hardly dropped when coated on the skin or the hair, and has a smooth feeling upon use without providing a dry and hard feeling on the skin and the hair.

As is evident from the above Examples, the anti-active oxygen agents according to this invention produce high inhibitory effects on the action of active oxygen species and can be easily prepared at low costs. They are physically and chemically stable. Accordingly, they can be used in anti-skin aging agents, cosmetics, pharmaceuticals or foods in order to prevent active oxygen species-induced disorders and diseases in human or other bodies as well as denaturation and deterioration of foods. Moreover, some of the anti-active oxygen compounds according to this invention have a UV absorptive power so that they are especially useful in cosmetics or the like.

Obviously, numerous modifications and variations of the present invention are possible in light of the above teachings. It is therefore to be understood that within the scope of the appended claims, the invention may be practiced otherwise than as specifically described herein.

This application is based on Japanese patent application 85133/1997 filed in the Japanese Patent Office on Apr. 3, 1997, the entire contents of which are hereby incorporated by reference.

What is claimed is:

1. An amino acid derivative represented by formula (I)

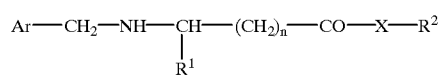

(I)

wherein

Ar represents a substituted or unsubstituted 2-hydroxyphenyl group, said substitution being selected from the group consisting of a halogen atom, a $C_{1-6}$alkyl group, a hydroxyl group, a hydroxy $C_{1-6}$alkyl group, a nitro group, a $C_{1-6}$alkoxyl group or a carboxyl group, $R^1$ represents a side chain of an amino acid, X represents —O— or —NH—, $R^2$ represents a $C_{8-22}$alkyl group, and n represents 0 or 1.

2. The amino acid derivative of claim 1, wherein $R^1$ is a side chain of an amino acid selected from the group consisting of glutamic acid, aspartic acid, cysteic acid, homocysteic acid, glycine, alanine, β-alanine, valine, leucine, isoleucine, phenylalanine, tryptophan, threonine, serine, homoserine, tyrosine, cysteine, methionine, glutamine, asparagine, lysine, ornithine, arginine and histidine.

3. The amino acid derivative of claim 1, wherein $R^1$ is a side chain of an amino acid selected from the group consisting of glycine, alanine and phenylalanine.

4. An active oxygen-resisting composition comprising:
i) an amino acid derivative represented by the following formula (I) or its salt

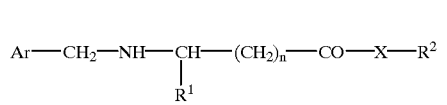

(I)

wherein

Ar represents a substituted or unsubstituted 2-hydroxyphenyl group or a pyridyl group, said substitution being selected from the group consisting of a halogen atom, a $C_{1-6}$alkyl group, a hydroxyl group, a hydroxy $C_{1-6}$alkyl group, a nitro group, a $C_{1-6}$alkoxyl group or a carboxyl group, $R^1$ represents a side chain of an amino acid, X represents —O— or —NH—, $R^2$ represents a $C_{8-22}$alkyl group, and n represents 0 or 1; and ii) a carrier.

5. The active oxygen-resisting composition of claim 4, comprising 0.01 to 10 wt. % of said amino acid derivative.

6. The active oxygen-resisting composition of claim 4, comprising 0.01 to 50 wt. % of said amino acid derivative.

7. The active oxygen-resisting composition of claim 4, further comprising a material selected from the group consisting of a wetting agent, a chelating agent, a crude drug; vitamins; hormones; an antihistamic agent, a skin astringent; a hair growth accelerator, a light-sensitive element; a beautifier, an antioxidant, an animal extract, a vegetable extract, an antiseptic a hormone an amino acid; a softener; a demulcent; a tough improver; a superfatting agent; a viscosity modifier; a pearling agent; an antiinflammatory agent; an ultraviolet absorber; a pH adjustor; a flavor; a coloring material and a mixture thereof.

8. The active oxygen-resisting composition of claim 4, wherein said carrier is an oil.

9. The active oxygen-resisting composition of claim 8, wherein said oil is selected from the group consisting of liquid paraffin, olive oil and a mixture thereof.

10. A skin anti-aging agent comprising the active oxygen-resisting composition of claim 4.

11. A cosmetic composition comprising the active oxygen-resisting composition of claim 4.

12. A skin external agent comprising the active oxygen-resisting composition of claim 4.

13. A method for inhibiting the generation of active oxygen species in a material, comprising applying an effective amount of an amino acid derivative represented by formula (I)

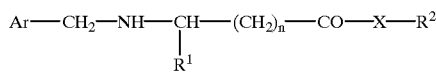

wherein
- Ar represents a substituted or unsubstituted 2-hydroxyphenyl group or a pyridyl group, said substitution being selected from the group consisting of a halogen atom, a $C_{1-6}$ alkyl group, a hydroxyl group, a hydroxy $C_{1-6}$ alkyl group, a nitro group, a $C_{1-6}$ alkoxyl group or a carboxyl group,
- $R^1$ represents a side chain of an amino acid,
- X represents —O— or —NH—,
- $R^2$ represents a $C_{8-22}$ alkyl group, and
- n represents 0 or 1.

14. A method for treatment against skin aging, comprising applying an effective amount of an amino acid derivative represented by formula (I)

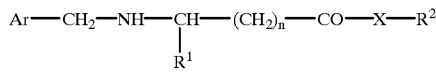

wherein
- Ar represents a substituted or unsubstituted 2-hydroxyphenyl group or a pyridyl group, said substitution being selected from the group consisting of a halogen atom, a $C_{1-6}$ alkyl group, a hydroxyl group, a hydroxy $C_{1-6}$ alkyl group, a nitro group, a $C_{1-6}$ alkoxyl group or a carboxyl group,
- $R^1$ represents a side chain of an amino acid,
- X represents —O— or —NH—,
- $R^2$ represents a $C_{8-22}$ all group, and
- n represents 0 or 1.

15. An amino acid derivative represented by formula (I)

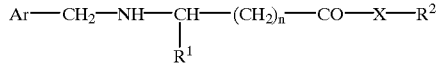

wherein
- Ar represents a substituted pyridyl group, said substitution being selected from the group consisting of a halogen atom, a $C_{1-6}$ alkyl group, a hydroxyl group, a hydroxy $C_{1-6}$ alkyl group, a nitro group, a $C_{1-6}$ alkoxyl group or a carboxyl group,
- $R^1$ represents a side chain of an amino acid,
- X represents —O— or —NH—,
- $R^2$ represents a $C_{8-22}$ alkyl group, and
- n represents 0 or 1.

16. The amino acid derivative of claim 15, wherein $R^1$ is a side chain of an amino acid selected from the group consisting of glutamic acid, aspartic acid, cysteic acid, homocysteic acid, glycine, alanine, β-alanine, valine, leucine, isoleucine, phenylalanine, tryptophan, threonine, serine, homoserine, tyrosine, cysteine, methionine, glutamine, asparagine, lysine, ornithine, arginine and histidine.

17. The amino acid derivative of claim 15, wherein $R^1$ is a side chain of an amino acid selected from the group consisting of glycine, alanine and phenylalanine.

18. An amino acid derivative represented by formula (I)

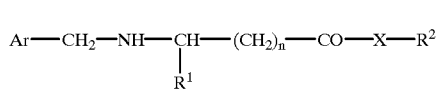

wherein
- Ar represents an unsubstituted pyridyl group,
- $R^1$ represents a side chain of an amino acid selected from the group consisting of glutamic acid, aspartic acid, cysteic acid, homocysteic acid, alanine, β-alanine, valine, leucine, isoleucine, phenylalanine, tryptophan, threonine, serine, homoserine, tyrosine, cysteine, methionine, glutamine, asparagine, lysine, ornithine, arginine and histidine,
- X represents —O— or —NH—,
- $R^2$ represents a $C_{8-22}$ alkyl group, and
- n represents 0 or 1.

19. The amino acid derivative of claim 18, wherein $R^1$ is a side chain of an amino acid which is alanine or phenylalanine.

* * * * *